United States Patent
Berber

(10) Patent No.: US 11,464,811 B2
(45) Date of Patent: Oct. 11, 2022

(54) MICROCAPSULES LOADED WITH PROBIOTICS AND PRODUCTION THEREOF

(71) Applicant: NANOMIK BIYOTEKNOLOJI A.S., Istanbul (TR)

(72) Inventor: Buse Berber, Istanbul (TR)

(73) Assignee: NANOMIK BIYOTEKNOLOJI A.S., Istanbul (TR)

(*) Notice: Subject to any disclaimer, the term of this patent is extended or adjusted under 35 U.S.C. 154(b) by 172 days.

(21) Appl. No.: 16/636,342

(22) PCT Filed: Aug. 15, 2018

(86) PCT No.: PCT/TR2018/050434
§ 371 (c)(1),
(2) Date: Feb. 4, 2020

(87) PCT Pub. No.: WO2019/125332
PCT Pub. Date: Jun. 27, 2019

(65) Prior Publication Data
US 2020/0155618 A1    May 21, 2020

(30) Foreign Application Priority Data
Aug. 21, 2017 (TR) .................. 2017/12406

(51) Int. Cl.
| | | |
|---|---|---|
| *A61K 35/741* | (2015.01) | |
| *A61K 8/9728* | (2017.01) | |
| *A61K 8/11* | (2006.01) | |
| *A61K 8/99* | (2017.01) | |
| *A61K 35/742* | (2015.01) | |
| *A61K 35/744* | (2015.01) | |
| *A61K 35/745* | (2015.01) | |
| *A61K 35/747* | (2015.01) | |
| *A01N 63/32* | (2020.01) | |
| *A01N 63/23* | (2020.01) | |
| *A01N 63/22* | (2020.01) | |
| *A01N 25/28* | (2006.01) | |
| *A23L 3/3571* | (2006.01) | |
| *A61K 8/04* | (2006.01) | |
| *A61K 9/50* | (2006.01) | |
| *A61K 36/064* | (2006.01) | |
| *A61Q 19/00* | (2006.01) | |
| *A61K 35/00* | (2006.01) | |

(52) U.S. Cl.
CPC ............ *A61K 35/741* (2013.01); *A01N 25/28* (2013.01); *A01N 63/22* (2020.01); *A01N 63/23* (2020.01); *A01N 63/32* (2020.01); *A23L 3/3571* (2013.01); *A61K 8/04* (2013.01); *A61K 8/11* (2013.01); *A61K 8/9728* (2017.08); *A61K 8/99* (2013.01); *A61K 9/5036* (2013.01); *A61K 9/5089* (2013.01); *A61K 35/742* (2013.01); *A61K 35/744* (2013.01); *A61K 35/745* (2013.01); *A61K 35/747* (2013.01); *A61K 36/064* (2013.01); *A61Q 19/00* (2013.01); *A23V 2002/00* (2013.01); *A61K 2035/115* (2013.01); *A61K 2800/10* (2013.01)

(58) Field of Classification Search
CPC .............. A01N 25/28; A01N 63/20–38; A61K 9/742–747
See application file for complete search history.

(56) References Cited

U.S. PATENT DOCUMENTS

| | | | |
|---|---|---|---|
| 2006/0008511 A1 | 1/2006 | Lin et al. | |
| 2007/0048295 A1* | 3/2007 | Chen ...................... | A61K 38/43 424/490 |
| 2012/0128821 A1 | 5/2012 | Nazzaro et al. | |

FOREIGN PATENT DOCUMENTS

| | | |
|---|---|---|
| CN | 101319210 A | 12/2008 |
| KR | 20090100033 A | 9/2009 |
| KR | 20100092923 A | 8/2010 |

OTHER PUBLICATIONS

Zanjani et al., "Microencapsulation of Probiotics by Calcium Alginate-gelatinized Starch with Chitosan Coating and Evaluation of Survival in Simulated Human Gastro-intestinal Condition", Iranian Journal of Pharmaceutical Research (2014), 13 (3): 843-852 (Year: 2014).*
https://sciencing.com/proper-conditions-autoclave-8204619.html (Year: 2022).*
https://ehs.princeton.edu/book/export/html/380 (Year: 2022).*
Yeung et al., "Microencapsulation in Alginate and Chitosan Microgels to Enhance Viability of Bifidobacterium longum for Oral Delivery", Front Microbiol. 2016; 7: 494 (Year: 2016).*
Whelehan et al., "Microencapsulation using vibrating technology", J Microencapsul. 2011;28(8):669-88 (Year: 2011).*
Krasaekoopt et al., "Evaluation of encapsulation techniques of probiotics for yoghurt", International Dairy Journal 13 (1) 3-13 (Year: 2003).*
Michael T. Cook, et al., Production and Evaluation of Dry Alginate-Chitosan Microcapsules as an Enteric Delivery Vehicle for Probiotic Bacteria, Biomacromolecules, May 16, 2011, p. 2834-2840, 12.
María Chávarri, et al., Microencapsulation of a probiotic and prebiotic in alginate-chitosan capsules improves survival in simulated gastro-intestinal conditions, International Journal of Food Microbiology, 2010, p. 185-189, 142.

* cited by examiner

Primary Examiner — Ruth A Davis
(74) Attorney, Agent, or Firm — Bayramoglu Law Offices LLC

(57) ABSTRACT

A production method of microencapsulated probiotics with chitosan-alginate polymers, the microcapsules loaded with probiotics obtained by this method and their use in food, agriculture and cosmetics. The microcapsules do not make alterations in the color and appearance of the product in which they are applied and have antifungal and anti-mycotoxin features.

10 Claims, No Drawings

MICROCAPSULES LOADED WITH PROBIOTICS AND PRODUCTION THEREOF

CROSS REFERENCE TO THE RELATED APPLICATIONS

This application is the national phase entry of International Application No. PCT/TR2018/050434, filed on Aug. 15, 2018, which is based upon and claims priority to Turkish Patent Application No. 2017/12406, filed on Aug. 21, 2017, the entire contents of which are incorporated herein by reference.

TECHNICAL FIELD

The invention is related to a production method of a microencapsulated form of probiotics with chitosan-alginate polymers, the microcapsules loaded with probiotics obtained by this method and their use in food, agriculture and cosmetics.

BACKGROUND

Mycotoxins are toxic metabolic products produced by some molds such as Aspergillus, Penicillium and Fusarium, which can be found in foods and agricultural products generally as a result of contamination. Mycotoxins are formed during the cultivation, storage, processing or transportation of foods cause varying degrees of toxicosis (mycotoxicosis) in humans and/or animals. Preventing the growth of mold in foods is difficult, however, the amount of these can be minimized during the processing and storage of foods by providing hygienic conditions. Forming of molds which produce toxins is an exceptional problem in the developing countries, because in these countries, there are no controlled storage conditions such as in the developed countries. Further, in tropical zones having warm and humid climate, the risk of mold growth in food increases.

After mycotoxins are formed, mycotoxins can be removed from food products by the use of binders. However, since this method is used after mycotoxin formation, it deteriorates the quality of the product, causes changes in taste and leads to chemical pollution. Also, since most of the binders used today are mycotoxin-specific, they do not present sufficient efficiency with products contaminated with more than one mycotoxin.

Due to reasons as such, the use of microorganisms which support consumer health and which have immune system-stimulating effects in the production of food and agricultural products has increased. It is known that the probiotics which constitute a significant group of these microorganisms play an important role in the prevention and treatment of gastrointestinal system disorders and formation of normal microflora. Use of probiotics in food stuff is longstanding. However, addition of probiotics directly into the food stuff product causes change in taste and quality of such food stuff product.

Also, it is known that the probiotic technology boosts the immune system, repairs the natural defense mechanism, prevents collagen structure damage and slows the aging process by providing the water balance of the skin.

The following U.S. patent applications may be related to the instant invention: US20060008511A1 and US20120128821A1.

SUMMARY

The invention is related to microcapsules obtained by microencapsulating endospore form of probiotics with chitosan-alginate polymers. Microcapsules loaded with said probiotics prevent mycotoxigenic molds and mycotoxins which the molds produce through biological struggle. A study was performed wherein encapsulation of probiotics was carried out especially in order to prevent probiotics from being damaged by gastric acid and in order to increase the quality in fermented products.

The resultant microcapsules loaded with probiotics related to the subject invention;
- Prevent the contamination of mycotoxin to food products at the rate of 95% compared to different combinations of probiotics,
- Do not cause any alteration in the color or appearance of the product to which they are applied,
- Affect many mycotoxin species of different types since they suppress the mold growth and stress mechanism in food and agricultural products,
- Have antifungal effect,
- Do not necessitate extra disinfection since they also have an antifungal effect on the product to which they are applied,
- Are natural and harmless,
- Provide protection in storage up to 360 days thus extending the shelf life of the product to which they are applied.

DETAILED DESCRIPTION

The present invention is related to chitosan-alginate microcapsules loaded with probiotics which present antifungal and anti-mycotoxin activity in fields such as food, agriculture, cosmetics and healthcare.
The production method of the microcapsules loaded with probiotic related to the invention contains the following steps of;
- Dissolving alginate in water at a ratio of 0.002-0.1% by weight,
- Autoclaving the alginate solution at a temperature of 110-130 degrees C., preferably at a temperature of 121 degrees C. and then sterilizing the same,
- Mixing probiotics with the alginate solution,
- Adding calcium chloride ($CaCl_2$) in an amount between 0.01-1.0 M, preferably 0.1 M to the probiotic-alginate mix and stirring,
- Dissolving chitosan in a 0.25-3.0% concentration by weight in 0.5-5% organic acid by volume (lactic acid, acetic acid, ascorbic acid, citric acid, tartaric acid, malic acid etc.), preferably in 1% organic acid (In this stage, the pH is adjusted between 3.5-7).
- Autoclaving the chitosan solution at a temperature of 110-130 degrees C., preferably at 121 degrees C. and then sterilizing the same,
- Thereafter, combining the 3:1 chitosan solution and the alginate-calcium chloride ($CaCl_2$) solution containing the probiotics in a container dropwise,
- Adding tween 80 (Polysorbate 80) to the chitosan solution-alginate-calcium chloride mix in a range of 0.01-2% by volume and stirring the mixture until homogenization is obtained.

The probiotics used in the invention are chosen from the microorganisms of; Bacillus laterosporus, Bacillus sphaericus, Bacillus subtilis, Bacillus coagulans, Streptococcus thermophilis, Azotobacter, Azospirillum, Agrobacterium, Gluconobacter, Flavobacterium, Herbaspirillum, Bacillus megaterium, Thiobacillus, B. polymyxa, B. brevis, B. licheniformis, B. circulans, B. cereus, B. thuringiensis, B. longum, B. breve, B. infantis, L. helveticus, L. rhamnosus, L.

plantarum, L. casei, L. acidophilus, Lactobacillus delbreckii, Lactobacillus ellobiosus, Lactobacillus lactis, Lactobacillu cidophilus, Lactobacillus reuteri, Lactobacillus brevis, Lactobacillus casei, Lactobacillus curvatus, Lactobacillus fermentum, Lactobacillus plantarum, Lactobacillus helveticus, Streptococcus cremoris, Streptococcus thermophiles, Streptococcus intemedius, Streptococcus lactis, Streptococcus diacetilactis, Enterococcus feacalis, Lactococcus spp, Lactococcus lactis subsp., Pediococcus spp., Pediococcus cerevisiae, Pediococcus acidilactici, Pediococcus pentosaceus, Bifidobacterium spp. Bifidobacterium animalis, Bifidobacterium adolecentis, Bifidobacterium bifidum, Bifidobacterium breve, Bifidobacterium infantis, Bifidobacterium longum, Leuconostoc spp. L. salivarius, L. paracasei, L. gasseri, L. reuteri, B. Bifidum, B. longum, B. infantis, Lb. delbrueckii, Lb. plantarum, Lb. pentosus, Lb. brevis, P. damnosus, Lb. collinoides, Lb. pentosus, Pediococcus spp., Lb. buohneri, Leuconostoc mesenteroides, Pedococcus pentosaceus, Lb. casei, Lb. kefir, Lb. acidophilus, Lb. helveticus, Lb. casei, Lb. bulgaricus, Lb. lactis, Lb. plantarum, Lb. brevis, Acetobacter spp., Streptococcus genera, Streptococcus spp., Streptococcus lactis, S. thermophilus, S. durans, S. cremoris, Lactobacillus alimentarus, L. Alimentarus, L. multaromicus, L. sanfrancisco, Lactococcus lactis ssp, S. cerevisia, Lactobacillus sakei, Lactobacillus alimentarius, Lactobacillus paralimentarius, Lactobacillus paracasei, Lactobacillus buchneri, Enterococcus faecium, Enterococcus mundtii, Enterococcus faecelis, Enterococcus casseliflavus, Lactobacillus pentosus, Enterococcus faecium, Pediococcus pentosaceus, Lactobacillus farciminis, Pichia kudriavzevii, Lactobacillus farciminis, Lactobacillus casei, Lactobacillus alimentarius, Pichia kudriavzevii, Candida humilis, L. lactis subsp. cremoris, Lb. delbrueckii subsp. lactis, Lb. helveticus, Lb. casei, Lb. delbrueckii subsp., Leuc. mesenteroides subsp. cremoris, Lb. Joshin, Lb. kefirenofacies, Lb. curvatus, P. acidilactici, P. pentosaceus, Lb. alimentarius, C. piscicola, Leuc. mesenteroides, P. acidilactici, P. cerevisiae, Lb. pentosus, P. acidilactici, T. halophilus, Lb. sanfransiscensis, Lb. farciminis, Lb. fermentum, Lb. amylovorus, Lb. reuteri, Lb. pontis, Lb. panis, Lb. alimentarius, W. cibaria, O. oeni, L. coryniformis, L. curvatus, L. jugurti, L. jensenii, L. bucheneri, L. cellobiosus, L. coprophilus, L. hilgardii, L. leichmannii, L. dextranicum, P. acidilactici, P. pentosaceus, S. thermophilus, L. lactis subsp. diacety lactis, L. lactis subsp. hordniae, L. garvieae, L. rafinolactis, V. fluvialis, V. salmoninarum, Leuconostoc sp., L. cremoris, L. dextranicum, L. mesenteroides, L. paramesenteroides, L. gelidum, L. carnosum, Carnobacterium sp., C. divergens, C. mobile, C. gallinarum, C. piscicola, Vagococcus sp., V. fluvialis, V. salmoninarum, L. garvieae, Lactococcus diacetylactis, Propionibacterium freudenreichii, Pediococcus sp, S. uvarum, Lb. coryniformis, Candida crusei, Weissella confusa, Hansenula silvicola, Debaryomyces hansenii, Trichosporon beigelli, Bacillus amyloliquefaciens, Torulopsis sp., Candida mycoderma, Lb. buchneri, P. acidilactici, Pediococcus pentasaceus, L. cellobiosus, E. mundtii/E. gallinarum, E. casseliflavus, P. urinae-equi, Lb. murinus, Candida milleri, E. burtonii, E. fibulinger, Issatchenkia orientalis, Candida pelliculosa, C. tropicalis, Pediococcus acidilactici, Pseudoplantarum, Pediococcus acidilactici, Pediococcus pentosaceus, Leuconostoc pseudomesenteroides, Weissella cibaria, Lb. paraplantarum, Issatchenkia orientalis, Candida glabrata, Pediococcus acidilactici, Kluyveromyces marxianus, Pichia kudriavzevii, Saccharomyces servazzi, Torulaspora delbrueckii, Kazachstania unispora, Saccharomyces barnettii.

Exemplary application of the product related to the invention to food and agricultural products is as follows:

10 ml of the solution containing $10^9$ cfu bacteria is mixed with 1 L water in order to provide protection against mycotoxin in the garden or during the storage period.

The same is applied on the products by means of a spraying method.

What is claimed is:

1. A method of producing polymeric microcapsules containing a probiotic which are protective against mold and mycotoxin formation, comprising the steps of:

1) dissolving alginate in water at a ratio by weight in a range of 0.002-0.1% to obtain an alginate solution,
2) autoclaving the alginate solution at a temperature range of 110-130 degrees C. and then sterilizing the alginate solution,
3) mixing a probiotic with the alginate solution to obtain a probiotic-alginate solution,
4) adding calcium chloride ($CaCl_2$) in a range of 0.01-1.0 M to the probiotic-alginate solution and stirring to obtain an alginate-calcium chloride solution,
5) dissolving chitosan in a 0.25-3.0% concentration range by weight in 0.5-5% organic acid by volume to obtain a chitosan solution,
6) autoclaving the chitosan solution at a temperature range of 110-130 degrees C., and then sterilizing the chitosan solution,
7) combining dropwise in a ratio of 3:1 the chitosan solution and the alginate-calcium chloride solution containing the probiotics in a container to obtain a chitosan-alginate-calcium chloride mixture,
8) adding Polysorbate 80 to the chitosan-alginate-calcium chloride mixture in a range of 0.01-2% by volume and stirring the mix until homogenization is obtained.

2. The method of claim 1, wherein the organic acid comprises at least one of lactic acid, acetic acid, ascorbic acid, citric acid, tartaric acid and malic acid.

3. The method of claim 1, wherein pH is in the range of 3.5-7 when the chitosan is dissolved in the organic acid.

4. The method of claim 1, wherein the alginate solution is autoclaved at a temperature of 121 degrees C. and then sterilized.

5. The method of claim 1, wherein the chitosan solution is autoclaved at a temperature of 121 degrees C. and then sterilized.

6. The method of claim 1, wherein 0.1 M calcium chloride ($CaCl_2$) is added to the probiotic-alginate solution and stirred.

7. The method of claim 1, wherein the chitosan is dissolved in 1% organic acid.

8. The method of claim 1, wherein the probiotics comprise at least one of bacteria and yeast.

9. The method of claim 8, wherein the probiotics are microorganisms selected from the group consisting of *Acetobacter* spp., *Agrobacterium, Azospirillum, Azotobacter, Bacillus amyloliquefaciens, Bacillus coagulans, Bacillus laterosporus, Bacillus megaterium, Bacillus sphaericus, Bacillus subtilis, Bifidobacterium* spp., *Bifidobacterium* adolecentis, *Bifidobacterium animalis, Bifidobacterium bifidum, Bifidobacterium breve, Bifidobacterium infantis, Bifidobacterium longum, Candida glabrata, Candida humilis, Candida krusei, Candida milleri, Candida mycoderma, Candida pelliculosa, Carnobacterium* sp., *Debaryomyces hansenii, Enterococcus casseliflavus, Enterococcus faecalis, Enterococcus faecium, Enterococcus gallinarum, Enterococcus mundtii, Gluconobacter Flavobacterium, Hansenula silvicola, Herbaspirillum, Issatchen-* kia orientalis, Kazachstania unispora, Kluyveromyces marxianus, Lactobacillus acidophilus, Lactobacillus alimentarius, Lactobacillus brevis, Lactobacillus buchneri, Lactobacillus casei, Lactobacillus cellobiosus, Lactobacillus curvatus, Lactobacillus delbrueckii, Lactobacillus delbrueckii subsp. Lactis, Lactobacillus farciminis, Lactobacillus fermentum, Lactobacillus helveticus, Lactobacillus lactis, Lactobacillus paracasei, Lactobacillus paralimentarius, Lactobacillus pentosus, Lactobacillus plantarum, Lactobacillus reuteri, Lactobacillus sakei, Lactococcus spp., Lactococcus diacetylactis, Lactococcus lactis ssp., Lactococcus lactis subsp. cremoris, Lactococcus lactis subsp. diacetylactis, Lactococcus lactis subsp. hordniae, Leuconostoc spp., Leuconostoc mesenteroides, Leuconostoc mesenteroides subsp. cremoris, Leuconostoc pseudomesenteroides, Oenococcus oeni, Pediococcus spp., Pediococcus acidilactici, Pediococcus cerevisiae, Pediococcus pentosaceus, Pediococcus urinae-equi, Pichia kudriavzevii, Propionibacterium freudenreichii, Pseudoplantarum, Saccharomyces barnettii, Saccharomyces servazzi, Streptococcus spp., Streptococcus cremoris, Streptococcus diacetylactis, Streptococcus intermedius, Streptococcus lactis, Streptococcus thermophilus, Thiobacillus, Torulaspora delbrueckii, Torulopsis sp., Trichosporon beigelli, Vagococcus spp., Vagococcus fluvialis, Vagococcus salmoninarum, Weissella cibaria, Weissella confusa.

10. The method of claim 1, wherein the probiotic comprises an endospore.

* * * * *